(12) United States Patent
Li

(10) Patent No.: US 11,109,944 B2
(45) Date of Patent: Sep. 7, 2021

(54) DEVICE FOR PROVIDING ENDODONTIC MATERIAL HAVING A CARTRIDGE INCLUDING AN ELECTRICALLY CONDUCTIVE HEATING LAYER

(71) Applicant: Tulsa Dental Products LLC, Tulsa, OK (US)

(72) Inventor: Nathan Y. Li, Mailbu, CA (US)

(73) Assignee: DENTSPLY SIRONA Inc., York, PA (US)

(*) Notice: Subject to any disclaimer, the term of this patent is extended or adjusted under 35 U.S.C. 154(b) by 261 days.

(21) Appl. No.: 15/701,061

(22) Filed: Sep. 11, 2017

(65) Prior Publication Data

US 2018/0071052 A1    Mar. 15, 2018

Related U.S. Application Data

(60) Provisional application No. 62/393,029, filed on Sep. 11, 2016, provisional application No. 62/393,030, filed on Sep. 11, 2016.

(51) Int. Cl.
*A61C 5/55*    (2017.01)
*A61C 5/62*    (2017.01)
(Continued)

(52) U.S. Cl.
CPC .............. *A61C 5/55* (2017.02); *A61C 1/0015* (2013.01); *A61C 5/62* (2017.02); *A61C 5/66* (2017.02);
(Continued)

(58) Field of Classification Search
CPC .... A61C 5/55; A61C 5/66; A61C 5/62; A61C 1/0015; A61K 6/0038; H05B 6/06; H05B 6/105; H05B 6/38
See application file for complete search history.

(56) References Cited

U.S. PATENT DOCUMENTS

| 4,265,618 A | * | 5/1981 | Herskovitz | .............. | A61C 5/50 |
| | | | | | 219/230 |
| 4,553,935 A | * | 11/1985 | Ueno | ................. | A61C 13/0028 |
| | | | | | 222/146.5 |

(Continued)

FOREIGN PATENT DOCUMENTS

WO      8700029 A1    1/1987

OTHER PUBLICATIONS

International Search Report; PCT/US2017/050983; Jan. 23, 2018 (completed); Mar. 19, 2018 (dated).
(Continued)

*Primary Examiner* — Nicholas D Lucchesi
*Assistant Examiner* — Hao D Mai
(74) *Attorney, Agent, or Firm* — Dentsply Sirona Inc.

(57) ABSTRACT

A cartridge includes a chamber structure configured to contain endodontic material. An electrically conductive heating layer is provided adjacent to the chamber structure. A first electrode is positioned at one side of the cartridge, with the first electrode being in electrical contact with the heating layer, and a second electrode is positioned at a second side of the cartridge, with the second electrode being in electrical contact with the heating layer. An outer sleeve encases the chamber structure, the heating layer, and the electrodes, with an air gap being formed between the outer sleeve and the heating layer.

22 Claims, 6 Drawing Sheets

(51) Int. Cl.
*A61C 5/66* (2017.01)
*A61C 1/00* (2006.01)
*A61K 6/54* (2020.01)
*H05B 6/06* (2006.01)
*H05B 6/10* (2006.01)
*H05B 6/38* (2006.01)

(52) U.S. Cl.
CPC ............ *A61K 6/54* (2020.01); *H05B 6/06* (2013.01); *H05B 6/105* (2013.01); *H05B 6/38* (2013.01)

(56) References Cited

U.S. PATENT DOCUMENTS

| | | | | |
|---|---|---|---|---|
| 4,582,488 A * | 4/1986 | Newman | ............... | A61C 5/55 433/81 |
| 4,684,344 A * | 8/1987 | Brockway | ............... | A61C 5/50 433/81 |
| 4,700,040 A * | 10/1987 | Driggers | ............... | B23K 3/053 219/85.1 |
| 4,704,088 A * | 11/1987 | Newman | ............... | A61C 5/55 433/81 |
| 4,953,755 A * | 9/1990 | Dennison | ............... | B05C 17/00536 222/109 |
| 6,794,612 B2 * | 9/2004 | Furtwangler | ...... | A61C 13/0028 219/227 |
| 9,033,706 B2 * | 5/2015 | Lee | ............... | A61C 5/50 433/81 |
| 9,375,291 B2 * | 6/2016 | Gramann | ............... | A61C 5/64 |
| 2003/0165793 A1 * | 9/2003 | Yobel | ............... | A61C 5/62 433/90 |
| 2004/0224282 A1 * | 11/2004 | Kazen | ............... | A61C 5/50 433/81 |
| 2005/0186531 A1 * | 8/2005 | Friedman | ............... | A61C 5/62 433/90 |
| 2006/0269893 A1 * | 11/2006 | Aloise | ............... | A61C 1/16 433/25 |
| 2006/0289493 A1 * | 12/2006 | Thomas | ............... | H05B 6/06 219/660 |
| 2008/0187883 A1 * | 8/2008 | Lee | ............... | A61C 5/50 433/81 |
| 2009/0258324 A1 * | 10/2009 | Yoshioka | ............... | A61C 17/0208 433/81 |
| 2010/0075276 A1 * | 3/2010 | Nakatsuka | ............... | A61C 5/62 433/89 |
| 2011/0165537 A1 * | 7/2011 | Jung | ............... | A61C 5/55 433/32 |
| 2015/0079538 A1 | 3/2015 | Li | | |
| 2017/0128158 A1 * | 5/2017 | Jung | ............... | A61C 5/55 |
| 2018/0200023 A1 * | 7/2018 | Lagarde | ............... | A61N 1/0548 |
| 2018/0214247 A1 * | 8/2018 | Sharma | ............... | A61C 5/50 |

OTHER PUBLICATIONS

International Preliminary Report on Patentability; PCT/US2017/050983; Jan. 23, 2018 (completed); Mar. 19, 2018 (dated).
Written Opinion of the International Searching Authority; PCT/US2017/050983; Jan. 23, 2018 (completed); Mar. 19, 2018 (dated).

* cited by examiner

DEVICE FOR PROVIDING ENDODONTIC MATERIAL HAVING A CARTRIDGE INCLUDING AN ELECTRICALLY CONDUCTIVE HEATING LAYER

This application claims priority to U.S. Provisional Application Nos. 62/393,029 and 62/393,030, both of which were filed on Sep. 11, 2016, and both of which are incorporated by reference in their entirety.

BACKGROUND

Field of the Invention

This invention is related to a device for providing endodontic material for use in a dental procedure, such as a root canal. In particular, this invention is related to an endodontic material application device that has a resistive heating element within a cartridge containing the endodontic material.

Related Art

Dental root canal treatments are a type of endodontics that are performed to remove infected dental pulp tissue inside the pulp chamber and root canals. After the infected dental pulp is removed, the vacant space is filled with an endodontic material. The ultimate objective of root canal treatment is to eliminate the infection inside the dental root system and to tightly seal or obturate, in three dimensions, the tiny openings at the end of the root canal (referred in the art as an apex). Dental root canal treatment therefore generally involves three stages: shaping, cleaning, and obturation (i.e., filling and sealing). Failure to completely seal the apex or the root canal in three dimensions leads to micro-leakage, which will lead to future bacteria colonization inside the root canal system, re-infection, and possible loss of the tooth. Indeed, micro-leakage is the most common cause of tooth failure.

The filling of the cleaned and shaped root canal space has been traditionally undertaken with a low-thermo endodontic compound, most often dental gutta percha. Previously, root canal treatment processes involved placement of the root canal filling and/or a sealing point or cone in a prepared root canal to plug the root canal, ideally in a manner to eliminate micro-leakage. However, conventional filling points and the process of application do not lend themselves well to providing a good seal of the root canal apex.

A popular method to apply dental root canal filling material into root canal space is warm gutta percha technique. Part of this technique is to preheat and soften gutta percha material, and then inject the softened gutta percha material into root canal space through a fine needle. Currently there different types of application devices for performing warm gutta percha technique. One such application device is similar to a conventional glue gun. This type of device has a heating barrel that is part of the gun-shaped applicator. An operator puts a piece of cylindrical rod shaped gutta percha into the heating chamber and attaches a fine needle in front of the barrel. After activating the heating element in the gun barrel to soften the gutta percha material, the dentist pulls a trigger to push a piston rod into the heated gun barrel, so as to squeeze the softened gutta percha material through the fine needle into the prepared root canal in the patient. However, since the gutta percha rod is directly inserted into heating chamber and softened before being dispensed, it leaves quite a sticky residue in the chamber. The residue must be cleaned with chemicals to prepare the application device for the next use. But the vapor from the cleaning chemicals might be harmful to, for example, expected mothers. Further, cross contamination among patients is a risk.

Other types of application devices have been designed to address some of the problems associated with the glue gun type devices. For example, some devices use gutta percha rods encased in disposable metal cartridges. Such cartridges generally have diameters of about 2.8 to 3.0 mm and are about 18 mm long. Ends of cartridges are connected to fine needles, and the other ends of the cartridges have a small nylon ball or pellet to seal off the end. Instead of a mechanical trigger configuration in the first type of applicator devices, the second type of applicator devices has a micro motor to move a piston forward to push gutta percha material out through the needle. This type of device is easier to clean, as the cartridge containing the gutta percha material is disposable.

The heating elements in both of the above-described types of devices share a common design, with heating pads and/or heating coils located on the body of the heating barrel. This heating element design can be problematic in in-vivo clinical applications. For example, with the placement of the heating coils on the body of the heating barrel, the barrel is bulky. It can therefore sometimes be hard to use the device to reach the back molar area of a patient's mouth. Another problem is that the heating mechanism might not be efficient because there may be air space between the endodontic material and the heating element provided in the heating chamber of the device. In this regard, gutta percha endodontic material generally needs to be heated to about 90° C. to about 125° C. in order to become soft enough to easily flow from the device. But, an operator will often need to set the device to heat to a much greater temperature in order to have sufficient heat transferred from the heating element to the cartridge containing the gutta percha. And the higher operating temperature can cause problems. For example, there is an increased risk of burning a patient when using the hot device. Thus, a thermo-protective sleeve is often used around the device body to protect the patient, with the sleeve in turn making the device even bulkier and difficult to maneuver. Moreover, given that the heating element in the application devices must be able to provide heat at higher temperature, the heating mechanism takes up more space, which further adds to the overall size of the device. Another problem is the heat transfer from the heating elements to the endodontic material is not consistent given the air space between the endodontic material and the heating chamber is not always consistent. In the event of excessive heat transfer, the endodontic material can become overheated and liquefy, causing the endodontic material to run off and possibly flow out of the needle before the operator is ready to use the device.

It is therefore desirable to develop a warm endodontic material application device that overcomes the drawbacks of the previous devices.

SUMMARY OF THE INVENTION

According to one aspect, the invention provides a cartridge that includes a chamber structure configured to contain endodontic material. An electrically conductive heating layer is provided adjacent to the chamber structure. The cartridge also includes a first electrode positioned at one side of the cartridge, with the first electrode being in electrical contact with the heating layer and a second electrode positioned at a second side of the cartridge, with the second electrode being in electrical contact with the heating layer. An outer sleeve encased the chamber structure, the heating layer, and the electrodes, with air gap being provided between the outer sleeve and the heating layer.

According to another aspect, the invention provides a cartridge including a chamber structure configured to contain the endodontic material and an electrically conductive heating layer provided adjacent to the chamber structure. The cartridge also includes a first electrode positioned at one side of the cartridge, the first electrode being in electrical contact with the heating layer, a second electrode positioned at a second side of the cartridge, the second electrode being in electrical contact with the heating layer, and a third electrode positioned between the first electrode and the second electrode along a length of the cartridge. An outer sleeve encases the chamber structure, the heating layer, and the electrodes.

According to yet another aspect, the invention provides an endodontic material application device that includes a handle assembly and a cartridge configured to contain endodontic material, with the cartridge being mounted to the handle assembly. The cartridge includes a chamber structure configured to contain the endodontic material, an electrically conductive heating layer provided adjacent to the chamber structure, a first electrode positioned at one side of the cartridge, the first electrode being in electrical contact with the heating layer, a second electrode positioned at a second side of the cartridge, the second electrode being in electrical contact with the heating layer, a third electrode positioned between the first electrode and the second electrode along a length of the cartridge, and an outer sleeve encasing the chamber structure, the heating layer, and the electrodes. The application device is configured such when a current is applied between the electrodes, more heat is generated in the heating layer between the first electrode and the third electrode than between the third electrode and the second electrode.

DETAILED DESCRIPTION OF THE INVENTION

This invention is related to an endodontic material application device that has a resistive heating element for heating the endodontic material. In the descriptions herein, the device will be described as being used in conjunction with an endodontic material, particularly gutta percha. These descriptions, however, should be understood as being merely exemplary. Indeed, as will be readily apparent to those skilled in the art, the application devices described herein could be used to apply other materials, including non-endodontic materials.

Figure 1:
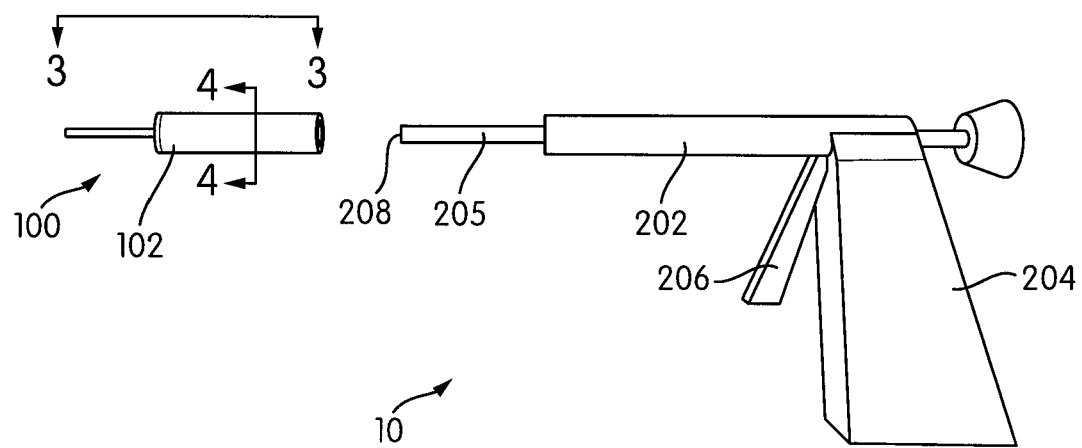
FIG. 1 is a view of an endodontic material application device according to an embodiment of the invention.

FIG. 1 is a view of an endodontic material application device 10 including a cartridge 100 and a handle assembly 200 according to an embodiment of the invention. The handle assembly 200 includes barrel 202 that is attached to a handle 204. The barrel 202 has a hollow internal chamber that is sized to receive a push rod 205. The push rod 205 can be made to move forward (i.e., away from the handle 204) by squeezing the trigger 206 towards the handle 204. As will be discussed below, the forward movement of the push rod 205 causes a plunger end 208 of the push rod 205 to force the endodontic material out of the cartridge 100.

As will be apparent to those skilled in the art, handle assemblies different than the specific handle assembly 200 shown in FIG. 1 could be used with the invention described herein. In this regard, the only functionality required for the handle assembly be that it facilitate the dispensing of the endodontic material from cartridges as described herein. In an alternative to the depicted embodiment, rather than using a force generated by the user, the handle assembly includes a motor that moves the push rod to thereby force the endodontic material out of cartridges. Such a motor could be a stepper type motor, with the stepper motor including gear teeth that mate with grooves provided on the push rod to move the push rod when the motor is powered on. An example of such a stepper motor is a piezo-electric motor, which is a small and energy efficient assembly capable of outputting power for use in forcing the endodontic material out of cartridges as described herein. In embodiments with a motor, the motor can be powered by a battery provided in the handle assembly, or the handle assembly can be provided with wiring to provide power to the piezo-electric motor. Yet another example of a handle assembly that can be used with a cartridge as described herein is shown in U.S. Patent Application Pub. No. 2015/0079538 A1, the disclosure of which is incorporated by reference in its entirety.

The cartridge 100 includes an outer sleeve 102, one end of which is attached to the barrel 202 of the handle assembly 200 (in FIG. 1, the cartridge 100 is shown detached from the barrel 202). In this regard, the end of the cartridge 100 can include a mechanical structure for connection to the handle assembly 200, such as a screw thread that receives a screw structure provided on the end of the barrel 202. Alternatively, the sleeve 102 can be sized to tightly fit over the outside of the end of the barrel 202, or vice-versa. Those skilled in the art will recognize numerous alternative ways that the cartridge 100 may be mounted to the barrel 202 of the handle assembly 200.

Figure 2:
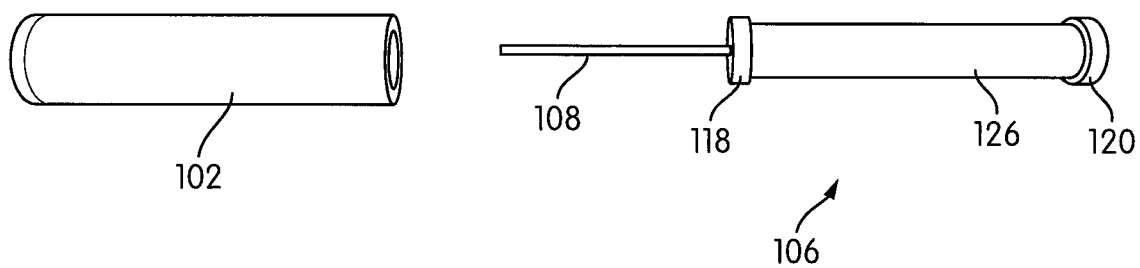
FIG. 2 is a view of parts of a cartridge according to an embodiment of the invention.
Figure 3:
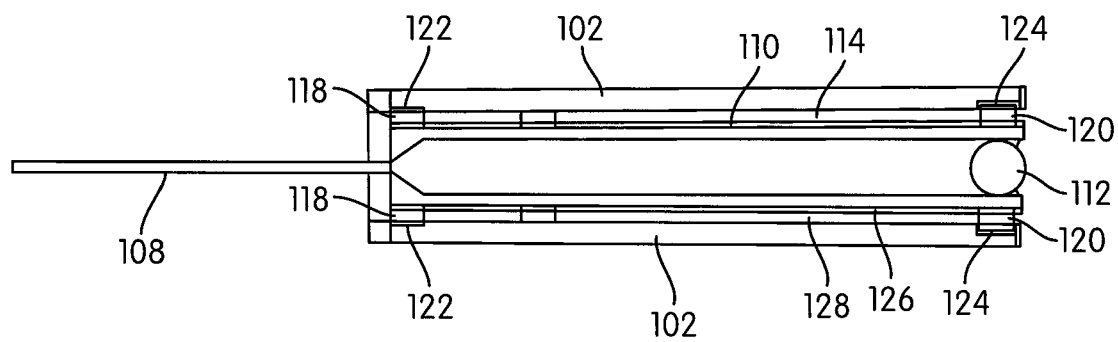
FIG. 3 is a cross-sectional view of a cartridge according to an embodiment of the invention as taken along line 3-3 in FIG. 1.
Figure 4:
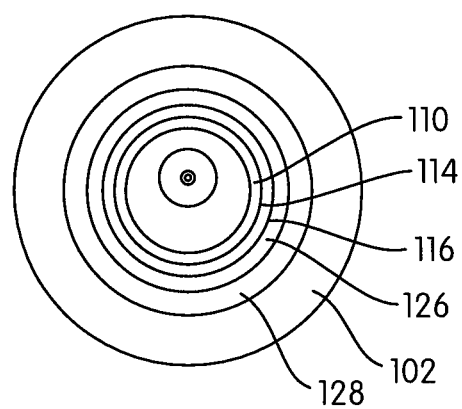
FIG. 4 is a cross-sectional view of a cartridge according to an embodiment of the invention as taken along line 4-4 in FIG. 1.

FIGS. 2, 3, and 4 are views of the cartridge 100. The cartridge 100 includes an endodontic material unit 106, a part of which is positioned within the sleeve 102. As will be discussed in detail below, the endodontic material unit 106 includes a chamber structure 110 for holding the endodontic material to be dispensed through a needle 108 that extends from the chamber structure 110. A part of endodontic material unit 106 including the chamber structure 110 is positioned within the sleeve 102, with the needle 108 extending from the end of the sleeve 102. The needle 108 can be attached to the chamber structure 110 by a threaded joint, welding, gluing, or other suitable attachment means. A sealing structure 112 (sometimes referred to as a ball seal) is movably provided within the chamber structure 110. The endodontic material is thereby sealed within the chamber structure 110 between the needle 108 and the sealing structure 112. When the application device 10 is used, the plunger 208 of the handle assembly 200 pushes the sealing structure 112 towards the needle 108 end of the cartridge 100, and the sealing structure 112 thereby pushes the endodontic material out of the cartridge 100 through the needle 108.

In embodiments of the invention, the chamber structure 110 can be made from a metallic material, such as stainless steel. As will now be described, additional layers of materials are formed outside of the chamber structure 110 to make up the endodontic material unit 106.

As shown in FIGS. 3 and 4, an electrical insulation layer 114 is applied to the outside surface(s) of the chamber structure 110. In particular embodiments of the invention, the electrical insulation layer can be a material such as epoxies (polyepoxides). The electrical insulation layer 114 can be applied to the chamber structure 110 by deposition, coating, silk screen printing, spray brushing, etc. In other embodiments, the electrical insulation layer can be in different forms, such as an insulating electrical tape.

An electrically conductive layer 116 is applied over the electrical insulation layer 114. As will be discussed below, during operation of the application device 10, a current is applied to the electrically conductive layer 116 is order to generate resistive heat in the layer 116, with that heat then heating the endodontic material contained in the adjacent chamber structure 110. As with the electrical insulation layer 114, the electrically conductive layer 116 may be applied using deposition, coating, silk screen printing, spray brushing, etc. The electrically conductive layer 116 could take many different forms. In particular embodiments, the electrically conductive layer 116 can be a material painted on the electrically insulation layer 114, with the paint including copper particles, carbon tubing, and/or silver particles. In a specific embodiment, the conductive paint contains copper particles having a size in the range of 600 nm to 30 μm and carbon tubing having a size in the range of 100 nm to 50 μm. In this regard, the proportion of metallic conducting elements in the electrically conductive layer 116 is based on the heating resistor value desired to produce the temperature needed for softening the endodontic material. For example, in embodiment of the invention wherein the endodontic material is gutta percha, an optimal working temperature range is from about 70° C. to about 200° C. To heat the gutta percha to these temperatures, an optimal resistor value for the electrically conductive layer 116 is between about 0.2 Ohm and about 2.0 Ohm.

A pair of electrodes 118 and 120 are used to provide the electrical current to the electrically conductive layer 116, with the electrodes 118 and 120 being provided in electrical contact with the conductive layer 116, and with the electrodes 118 and 120 being provided towards opposite sides of the endodontic material unit 106. The electrodes 118 and 120 are also in electrical contact with corresponding electrodes 122 and 124 provided in the sleeve 102, as will be described below. The electrodes 118 and 120 may be, for example, copper rings.

A thermal insulation layer 126 is provided on the electrically conductive layer 116 between the electrodes 118 and 120. As with the electrically insulating and electrically conductive layers 114 and 116, the thermal insulation layer 126 can be in a variety of different forms and can be applied using a variety of techniques. In a specific embodiment of the invention, the thermal insulation layer 126 is TEFLON® (i.e., polytetrafluoroethylene), which is a thermally insulating material made by the Chemours Company of Wilmington, Del.

As noted above, the endodontic material unit 106 is provided within the sleeve 102, with the needle 108 extending from an end of the sleeve 102. The sleeve 102 can be formed, for example, from a plastic material. An example of such a plastic material is ZYTEL® HTN92G45DH2, which is a polyamide resin with glass filler beads made by E. I. du Pont de Net ours and Company of Willington, Del. As shown in FIG. 4, the inside surface of the sleeve 102 is spaced from the thermal insulation layer 124. Thus, an air gap 128 is formed between the almost all of the endodontic material unit 106 and the sleeve 102. The air gap 128 functions as a highly effective thermal insulator to prevent the sleeve 102 from becoming significantly heated when the endodontic material contained in the chamber structure 106 is heated by the resistive heating in the electrically conductive layer 116. This is advantageous as the outer sleeve 102 may come into contact with a patient's mouth when the application device 10 is used to apply the endodontic material, and the sleeve 102 could thereby cause a burn if the sleeve 102 is too hot.

By using an integrated electrically conductive layer as the heating element in the cartridges according to the invention, and by having integrated insulating layers and an air gap to provide further insulation, the size of the endodontic material cartridges can be significantly reduced compared to previous heated endodontic material cartridges. For example, with a cartridge configuration as described herein, the cartridge may have a diameter of about 10 mm, or even less, whereas previous heated endodontic material cartridges had diameters of greater than about 20 mm. This difference is significant because, as discussed above, the cartridge part of the application device must often be maneuvered in the patient's mouth.

As also noted above, and as shown in FIG. 4, the electrodes 118 and 120 provided in the endodontic material unit 106 are electronically contacted to electrodes 122 and 124 provided on the inside surface of the sleeve 102. The electrodes 122 and 124 in turn are provided with an electrical connection to further electrodes (not shown) provided at the end of the sleeve 102 that is adjacent to the barrel 202 of the handle assembly 200. When the sleeve 102 is formed from plastic, the electrodes and other electrical connections may be imbedded in an injection molding process used to form the sleeve 102. As such, an electrical power source (e.g., a battery) in the handle assembly 202 can provide the current for the resistive heating in the electrically conductive layer 116 by way of the electrodes 118, 120, 122, and 124. In this regard, the electrical connection between the cartridge 100 and the handle assembly 200 may be similar to the electrical connection between the cartridge and the handle assembly described in the aforementioned U.S. Patent Application Pub. No. 2015/0079538 A1. Further, appropriate switches and/or control electronics may be provided with the cartridge 100 and handle assembly 200 combination, such as a control unit in the handle assembly 200. Those skilled in the art will be able will be able to easily implement such controls to achieve the operational objectives using the application device 10 as described herein. Moreover, those skilled in the art will recognize numerous alternatives for providing power to the electrically conductive layer 116 in the cartridge 100. For example, instead of providing the power supply in the handle assembly 200, the endodontic material application device 10 could be provided with wiring for connection to an external power source.

In order to control the heating temperature of the endodontic material in the cartridge 100, a control unit can be configured to determine the power to be supplied to the cartridge 100 based signals received from the cartridge 100.

For example, a control unit provided in the handle assembly 200 can adjust the working temperature based on a particular cartridge's resistor value—the control unit could determine the resistor value based on feedback when a specific amount of power is supplied to the cartridge. Further, the control unit could also control the heating of the cartridge 100 based a particular cartridge's endodontic material viscosity rating, e.g., the particular cartridge could include a signal sending device that the control unit detects when the cartridge is installed on the handle assembly 200.

The cartridge 100 with the needle 108, endodontic chamber structure 106, and the sleeve 102 may be disposable after the endodontic material is dispensed from the cartridge 100. Hence, the handle assembly 200, as described above, may be used with another cartridge. It should be noted, however, that while the combination of the needle 108, chamber structure 106, and sleeve 102 are referred to herein as a "cartridge," in other embodiments different combinations of these and other structures can be combined to be used as cartridges for each use with other structures being reusable with the application device 10. For example, in an alternative embodiment the chamber structure 106 and the needle 108 are provided together as a disposable unit (i.e., a "cartridge"), while the sleeve 102 is a reusable part of the application device 10. In such an embodiment, the chamber structure 106 and the needle 108 are made easily detachable from the sleeve 102. In another embodiment, the needle 108 and the sleeve 102 are made detachable from the chamber structure 106 such that the needle 108 and sleeve 102 are reusable parts of the application device 10 while the chamber structure 106 is a disposable part (i.e., a "cartridge").

Figure 5:
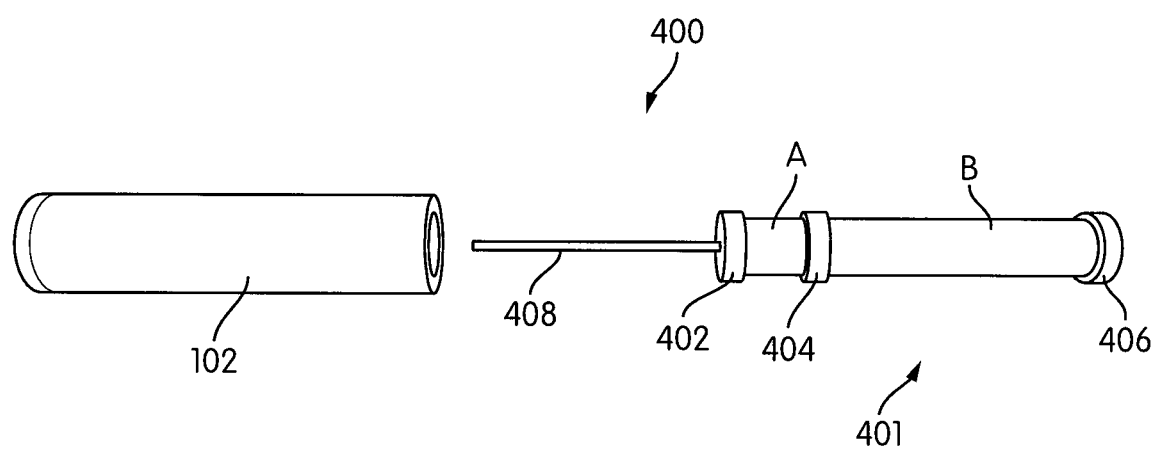
FIG. 5 is a view of parts of a cartridge according to another embodiment of the invention.

FIG. 5 shows a cartridge 400 with endodontic material unit 401 according to alternative embodiments of the invention. This endodontic material unit 401 has a similar configuration to the endodontic material unit 106 described above. For example, the endodontic material unit 401 has an outer sleeve 102 into which the endodontic material unit 406 is fit and the unit 401 includes an electrically conductive heating layer to heat an endodontic material chamber structure. The endodontic material unit 401 is different from the unit 106 described above in that the endodontic material unit 401 includes three electrodes 402, 404, and 406. Two of the electrodes 402 and 404 are provided closer to the needle 408, while the other electrode 406 is provide at the opposite side of the endodontic material unit 401. In a specific embodiment, the two electrodes 402 and 404 are positive electrodes, while the electrode 406 is a negative electrode. With the three electrode 402, 404, and 406 configuration, two different heating zones A and B can be created in the endodontic material unit 401. And different heating levels can be achieved in the two heating zones A and B by adjustment of the power supplied to the electrodes 402 and 404. In particular, greater heating can be provided in the electrical conductive layer in zone A than the electrically conductive layer in zone B. By having greater heating in zone A, it is ensured that the endodontic material is sufficiently softened as it approaches the needle 108.

As an additional or alternative way to ensure that the endodontic material is softened at the end of the chamber structure adjacent to the needle, in embodiments of the invention the walls of chamber structure itself can be made thicker at the end adjacent to the needle. The thicker end of the chamber structure will provide a greater heat sink, and thereby provide more heat to the endodontic material as the material approaches the needle.

In other embodiments of the invention, a two zone heating effect is achieved using just two electrodes as in the endodontic material unit 106 described above. In these embodiments, the electrically conductive layer is provided with different resistive values along the length of the endodontic material unit 106. In this case, with the part of the electrically conductive layer near the needle having a resistance value that generates more heat the part of the electrically conductive layer that is further from the needle. Thus, it is ensured that the endodontic material is sufficiently softened as it approaches the needle. In the case where gutta percha is the endodontic material used in the cartridge, the resistive value of the electrically conductive layer near the needle can be 0.2 Ohm, while the resistive value of the rest of the electrically conductive layer is 0.5 Ohm. Those skilled in the art will recognize the ways that the resistive values of parts of the electrically conductive layer can be adjusted, e.g., by adjustment of the proportion of metallic conducting elements in the different parts of the electrically conductive layer. Additionally, further embodiments of the invention include both three electrodes and different resistive value parts of the electrically conductive layer in order create different heating zones.

In yet another embodiment of the invention, the body of the endodontic material unit is primarily formed from a non-metallic material; that is, the endodontic material chamber structure, thermal resistive layer, and electrically conductive layer parts of the cartridges described above are formed from non-metallic materials. Such non-metallic materials include injection molded ceramics or injected molded composite materials. In embodiments with a non-metallic endodontic material unit, an electro-thermal conductive heating material can be added to the non-metallic material, such as carbon, gold, silver, chromium, palladium, platinum, copper, or molybdenum. In specific embodiments, molybdenum disilicide ($MoSi_2$) at a concentration of about 15% to about 50% of the total weight of the endodontic material chamber structure (the total weight not including coating layers, needle, sealing structure, and endodontic material). In other embodiments, 100 nm to 1 μm carbon tubes are used, with the carbon tubes being in a concentration range of about 5% to about 30% of the total weight of the endodontic material chamber structure. As will be appreciated by those skilled in the art, the concentrations of molybdenum disilicide, carbon tubes, or other thermal conductive heating elements can be selected based on the power level to be used and the required working temperature. In the non-metallic cartridge body embodiments, electrodes can be applied in the same manner as the embodiments described above, and a further thermal resistive layer can be applied to the body in the same manner as the embodiments described above. Also, a sleeve can be used over the non-metallic endodontic material unit.

Figure 6:
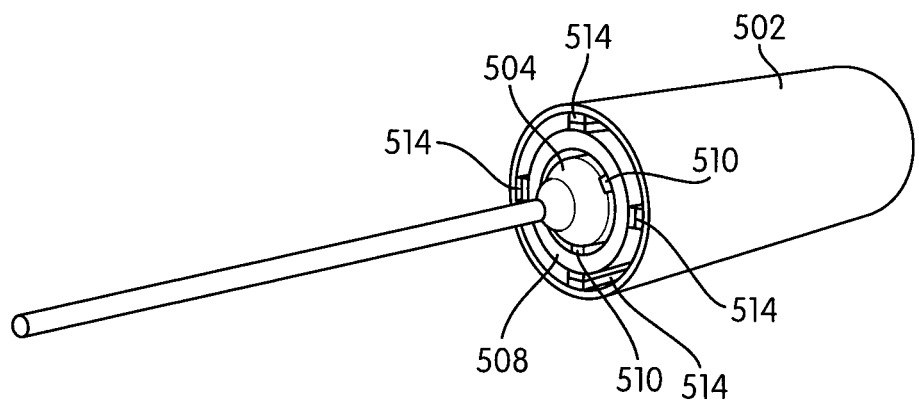
FIG. 6 is a view of a cartridge according to a further embodiment of the invention.
Figure 7:
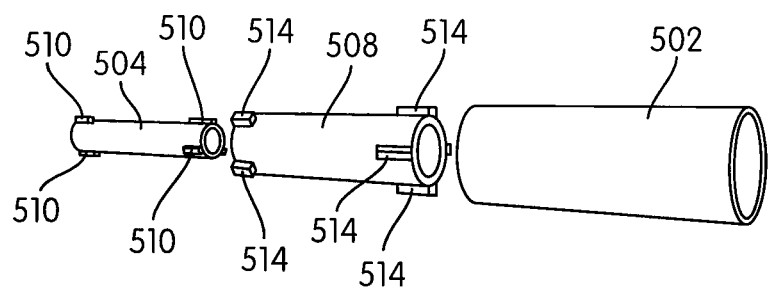
FIG. 7 is a view of parts of the cartridge depicted in FIG. 6.

FIGS. 6 and 7 depict a cartridge 500 according to a further embodiment of the invention. In this embodiment, an outer sleeve 502 and an endodontic material unit 504 having an endodontic material chamber structure, electrically insulation layer, and an electrical conduction (heating) layer, are formed as in the embodiments described above. In this embodiment, however, an insulating sheath 508 is provided between the endodontic material unit 504 and the sleeve 502. The insulating sheath 508 can be made from a variety of materials, and in particular, plastic materials. A plurality of spacer pegs 510 are formed on the outer surface of the endodontic material unit 504, and, similarly, a plurality of spacer pegs 514 are formed on the outer surface of the insulating sheath 508. Thus, the endodontic material unit 504 is spaced from the insulating sheath 508, and the insulating sheath 508 is spaced from the outer sleeve 502.

The spaces between the structures become thermally insulating air gaps 516 and 518. The combination of air gaps 516 and 518 and insulating sheath 508 provides highly effective thermal insulation such that the sleeve 502 is not significantly heated when the endodontic material unit 504 is heated. As noted above, this is advantageous because the outer sleeve 502 may come into contact with a patient's mouth when the application device is used to apply the endodontic material, and the outer sleeve 502 could cause a burn if the sleeve 502 is too hot. It should be noted that electrodes can also be provided in the sleeve 502 and in the endodontic material unit 504 in a manner similar to the embodiments described above. Further, the insulating sheath 508 may contain a locking ring to secure the endodontic material unit 504, for example, some of the pegs 510 can be set to the locking ring as the endodontic material unit 504 is inserted into the sheath 508, with the pegs 510 then being set in a locked position by the locking ring when the endodontic unit 504 is rotated in the sheath 508.

With the invention described herein, an endodontic material application device can be provided with a compact cartridge having an integrated heating element in the form of electrically conductive layer within the cartridge. Such an integrated heating element layer allows for the size of the cartridge to be reduced compared to previous heated endodontic material cartridges, which in turn improves the usability of the application device by making the device more easily maneuverable in a patient's mouth. Moreover, the heat generated in the cartridge with the integrated heating element layer is more consistent than previous heated endodontic material cartridges. The application device is easily adaptable for cartridges having different heating characteristics and different endodontic materials. Still further, the heat is insulated in the device, which reduces the risk of the outside surfaces of the device causing a burn if the device contacts the patient.

Although this invention has been described in certain specific exemplary embodiments, many additional modifications and variations would be apparent to those skilled in the art in light of this disclosure. It is, therefore, to be understood that this invention may be practiced otherwise than as specifically described. Thus, the exemplary embodiments of the invention should be considered in all respects to be illustrative and not restrictive, and the scope of the invention to be determined by any claims supportable by this application and the equivalents thereof, rather than by the foregoing description.

INDUSTRIAL APPLICABILITY

The devices described herein can be used for commercial products for use in dental procedures, such as devices used in endodontics. The devices described herein therefore clearly have industrial applicability.

The invention claimed is:

1. A cartridge comprising:
an endodontic material unit having a chamber structure configured to contain endodontic material;
an electrical insulation layer provided on an outer surface of the chamber structure along a length of the endodontic material unit; and
an electrically conductive heating layer having at least two zones of different resistive values provided on the electrical insulation layer, along a length of the endodontic material unit;
a first electrode positioned at one side of the endodontic material unit, the first electrode being in electrical contact with the heating layer;
a second electrode positioned at a second side of the endodontic material unit, the second electrode being in electrical contact with the heating layer;
an outer sleeve encasing the endodontic material unit including the chamber structure, the heating layer, and the electrodes;
a thermal insulation layer provided on the heating layer and between the electrodes;
wherein an air gap is provided between the thermal insulation layer and the outer sleeve.

2. The cartridge according to claim 1, wherein the outer sleeve includes an electrode in electrical contact with the first electrode and another electrode in electrical contact with the second electrode.

3. The cartridge according to claim 1, further comprising a third electrode positioned between the first electrode and the second electrode, the third electrode being in electrical contact with the heating layer.

4. The cartridge according to claim 3, wherein the heating layer has a first electrical resistance between the first electrode and the third electrode, and a second electrical resistance between the third electrode and the second electrode, with the first electrical resistance being different than the second electrical resistance.

5. The cartridge according to claim 1, wherein the electrically conductive heating layer having the at least two zones of different electrical resistances along the length of the endodontic material unit, between the first electrode and the second electrode.

6. The cartridge according to claim 1, further comprising a needle extending from an end of the cartridge such that the endodontic material may move from the chamber structure to the needle.

7. The cartridge according to claim 6, wherein the resistive value of the electrically conductive layer near the needle is 0.2 Ohm and the resistive value of the rest of the electrically conductive layer is 0.5 Ohm.

8. The cartridge according to claim 1, further comprising endodontic material contained in the chamber structure of the endodontic material unit.

9. The cartridge according to claim 8, wherein the endodontic material is gutta percha.

10. The cartridge according to claim 1, wherein the air gap acts as a thermal insulator to prevent the outer sleeve from becoming heated when the endodontic material contained in the chamber structure is heated.

11. The cartridge according to claim 1, wherein the cartridge has a diameter of not more than 10 mm.

12. An endodontic application device comprising:
a cartridge that includes:
an endodontic material unit having a chamber structure configured to contain endodontic material;
an electrical insulation layer provided on an outer surface of the chamber structure along a length of the endodontic material unit; and
an electrically conductive heating layer having at least two zones of different resistive values provided on the electrical insulation layer, along a length of the endodontic material unit;
a first electrode positioned at one side of the endodontic material unit, the first electrode being in electrical contact with the heating layer;

a second electrode positioned at a second side of the endodontic material unit, the second electrode being in electrical contact with the heating layer;

an outer sleeve encasing the endodontic material unit including the chamber structure, the heating layer, and the electrodes;

a thermal insulation layer provided on the heating layer and between the electrodes; and a needle extending from an end of the cartridge such that the endodontic material may move from the chamber structure to the needle;

wherein an air gap is provided between the thermal insulation layer and the outer sleeve; and a handle assembly to which the cartridge is attached, handle assembly including a plunger configured to act on part of the cartridge to force endodontic material contained in the chamber structure out of the cartridge through the needle.

13. A cartridge comprising:

an endodontic material unit having a chamber structure configured to contain endodontic material;

an electrically conductive heating layer provided to an outer surface of the chamber structure along a length of the endodontic material unit;

a first electrode positioned at one side of the endodontic material unit, the first electrode being in electrical contact with the heating layer;

a second electrode positioned at a second side of the endodontic material unit, the second electrode being in electrical contact with the heating layer;

a third electrode positioned between the first electrode and the second electrode along a length of the endodontic material unit; and an outer sleeve encasing the endodontic material unit including the chamber structure, the heating layer, and the electrodes.

14. The cartridge according to claim 13, wherein an air gap is provided between the outer sleeve and the heating layer.

15. The cartridge according to claim 13, further comprising:

a thermal insulation layer provided on the heating layer and between the first, second, and third electrodes, wherein the air gap is provided between the thermal insulation layer and the outer sleeve.

16. The cartridge according to claim 13, further comprising a needle extending from an end of the chamber structure such that the endodontic material may move from the chamber structure to the needle.

17. The cartridge according to claim 13, further comprising endodontic material contained in the chamber structure of the endodontic material unit.

18. The cartridge according to claim 17, wherein the endodontic material is gutta percha.

19. An endodontic material application device comprising:

a handle assembly; and a cartridge for containing an endodontic material, the cartridge being mounted to the handle assembly, and the cartridge comprising:

an endodontic material unit having a chamber structure configured to contain endodontic material;

an electrically conductive heating layer provided to an outer surface of the chamber structure along a length of the endodontic material unit;

a first electrode positioned at one side of the endodontic material unit, the first electrode being in electrical contact with the heating layer;

a second electrode positioned at a second side of the endodontic material unit, the second electrode being in electrical contact with the heating layer;

a third electrode positioned between the first electrode and the second electrode along a length of the endodontic material unit; and an outer sleeve encasing the endodontic material unit including the chamber structure, the heating layer, and the electrodes, wherein the device is configured such when a current is applied between the electrodes, more heat is generated in the heating layer between the first electrode and the third electrode than between the third electrode and the second electrode.

20. The endodontic application device according to claim 19, wherein an air gap is provided between the outer sleeve and the heating layer in the cartridge.

21. The endodontic application device according to claim 19, further comprising:

a thermal insulation layer provided on the heating layer in the cartridge and between the first, second, and third electrodes, wherein the air gap is provided between the thermal insulation layer and the outer sleeve.

22. A cartridge comprising:

an endodontic material unit having a chamber structure configured to contain endodontic material;

an electrical insulation layer provided on an outer surface of the chamber structure along a length of the endodontic material unit;

an electrically conductive heating layer provided on the electrical insulation layer along a length of the endodontic material unit;

a first electrode positioned at one side of the endodontic material unit, the first electrode being in electrical contact with the heating layer;

a second electrode positioned at a second side of the endodontic material unit, the second electrode being in electrical contact with the heating layer;

an outer sleeve encasing the endodontic material unit including the chamber structure, the heating layer, and the electrodes, an insulating sheath provided between the endodontic material unit and the outer sleeve;

a first plurality of spacer pegs provided on an outer surface of the endodontic material unit, such that a first thermally insulating air gap is created between the endodontic material unit and the insulating sheath;

a second plurality of spacer pegs provided on an outer side of insulating sheath, such that a second thermally insulating air gap is created between the insulating sheath and the outer sleeve; and a needle extending from an end of the chamber structure such that the endodontic material may move from the chamber structure to the needle;

wherein the outer sleeve includes an electrode in electrical contact with the first electrode and another electrode in electrical contact with the second electrode;

wherein the insulating sheath further comprises a locking ring to secure the endodontic material unit; and wherein some of the first plurality of spacer pegs provided on the outer surface of the endodontic material unit is set to the locking ring as the endodontic material unit is inserted into the insulating sheath, with the spacers pegs then being set in a locked position by the locking ring when the endodontic unit is rotated in the insulating sheath.

\* \* \* \* \*